Aug. 1, 1961 J. F. SCHLOEN Plant Pat. 2,076
LILAC PLANT
Filed Aug. 22, 1960
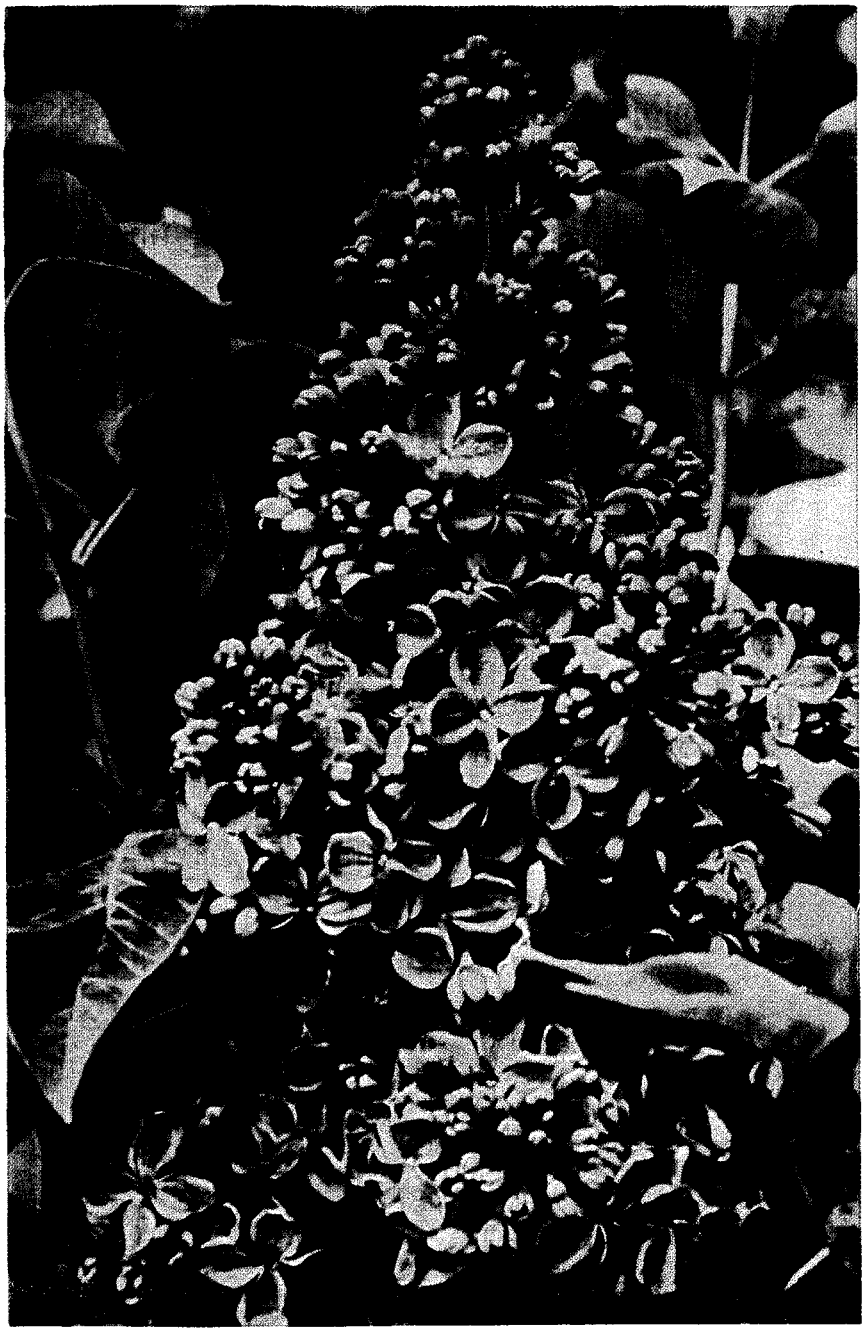
INVENTOR
John F. Schloen
BY Robb & Robb
ATTORNEYS United States Patent Office Plant Pat. 2,076
Patented Aug. 1, 1961

2,076
LILAC PLANT

John F. Schloen, Brooklin, Ontario, Canada

Filed Aug. 22, 1960, Ser. No. 51,246
1 Claim. (Cl. 47—60)

The present invention relates to a new and distinct variety of lilac plant of the French hybrid type as related to the species *Syringa vulgaris*, which originated as a seedling resulting from the planting of seeds derived from various sources and of unknown parentage. These seeds were planted on cultivated property as a part of an experimental program conducted for the purpose of creating new and improved lilac varieties.

As the result of the experimental program referred to above, the present variety was selected as the most outstanding by virtue of the fact that it is substantially different from any other lilac variety of which I am aware, as evidenced by the following unique combination of characteristics:

(1) A rapid and vigorous habit of plant growth as indicated by a growth of as much as 5 feet in one growing season in the case of a 1-year graft, without special fertilization or other special treatment or care;

(2) Large, ovate, heart-shaped foliage, which in itself is rather unusual as compared with the normally slender leaves of most lilac varieties;

(3) A distinctive dark grey-green color and leathery texture of the foliage;

(4) Exceptionally large florets ranging from 1¼ to 1½ inches in diameter, and a compact arrangement of the florets in individual flower heads or spikes;

(5) Individual flower heads composed of unusual combinations of florets mostly having 4 but sometimes 5 petals each;

(6) An unusual giant size of the flower heads ranging from 11 inches to 14 inches in length;

(7) A distinctive Deep Reddish Purple general color tonality of the flowers and good persistence of the flower color without fading;

(8) Recessed bright yellow stamens;

(9) Exceptionally good hardiness to frost, as indicated by survival without injury when subjected to temperatures as low as 20° F. below zero;

(10) An unusually prolonged retention of the flower petals without dropping;

(11) A gradual opening habit of the flowers, beginning at the bottom of each spike; and

(12) A strong and pleasing fragrance.

Asexual reproduction of this new lilac variety by both budding and grafting, as performed by me at Brooklin, Ontario, Canada, shows that the foregoing characteristics and distinctions come true to form and are established and transmitted through succeeding propagations.

The accompanying drawing shows typical specimens of the flowers and foliage of my new lilac variety as depicted in color.

The following is a detailed description of the new variety, with color terminology in accordance with the Nickerson Color Fan, published by Munsell Color Company Incorporated, of Baltimore, Maryland, U.S.A., except where general color terms of ordinary dictionary significance are obvious, all based upon observations of specimens grown in my nurseries at Brooklin, Ontario, Canada:

Type: Hardy; bush; outdoor; seedling; for garden decoration.

Parentage: A seedling of unknown parentage.

Propagation: Holds its distinguishing characteristics through succeeding propagations by both budding and grafting.

*Flower*

Flowers borne: Several to stem; in large clusters; on strong stems.

Quantity of bloom: Free, outdoors.

Continuity: Continuously for a period of about 3 weeks each year, beginning about 1 week later than the variety "Charles Joly" (unpatented).

Fragrance: Strong and pleasant.

Flower buds: Rounded form; with crinkled petals.

Bloom:

*Size.*—Very large; trusses range in length from 11 inches to 14 inches, with trusses composed of florets, each ranging in size from 1¼ to 1½ inches in diameter, and averaging 1⅜ inches.

*Petalage.*—Single; sometimes 4 and sometimes 5 petals in each floret; petals sometimes arranged regularly and sometimes irregularly.

*Form.*—Florets are cupped and globular at first, but became very flat, with high center; petals at first are cupped and rolled inward, but later become flat and rolled outward at maturity.

Petals:

*Texture.*—Thick; with inside absorbing light and having a velvety appearance, and with outside reflecting light similar to satin; no hairy bloom on petals, but quite smooth to the touch.

*Shape.*—Oval; usually with one notch.

*Color.*—From Deep Purplish Red, Plate 7.5RP 3/9 to Deep Reddish Purple, Plate 2.5RP 3/8, and sometimes slightly darker.

*Reproductive organs*

Stamens: Few; arranged regularly; tucked in carolla tube. Color—Brilliant Yellow, Plate 5Y 9/9.

Ovaries: All enclosed in calyx.

Seeds: Few; large.

*Plant*

Foliage: Abundant; large; heart-shaped; leathery.

*Size (when mature).*—Average 7 inches long and 5 inches wide.

*Color.*—Mature—from Moderate Olive Green, Plate 5GY 4/3 to Greyish Olive Green, Plate 5GY 3/2.

Young—from Moderate Olive Green, Plate 5GY 4/3 to Moderate Yellow Green, Plate 5GY 5/6.

Growth: Bushy; upright; vigorous.

*General observations*

The only variety of which I am aware that has large florets of a size generally comparable to my new variety is the variety known as "Clark's Giant Hybrid" (unpatented). However, the flower heads of my new variety are longer and more compact, without interspersed leaves that are typical of "Clark's Giant Hybrid." The flowers of "Clark's Giant Hybrid" are gentian blue in color and composed of standard 4-petaled florets, while those of my new variety are a rich, non-fading red color and composed of florets having both 4 and 5 petals each.

I claim:

A new and distinct variety of lilac plant, substantially as herein shown and described, characterized particularly as to novelty by the unique combination of a rapid and vigorous habit of plant growth, large heart-shaped leaves, a distinctive dark grey-green color and leathery texture of the foliage, exceptionally large individual florets each having 4 or 5 petals, a compact arrangement of the florets in the individual flower heads or spikes, exceptionally large flower heads or trusses, a distinctive Deep Reddish Purple general color tonality of the flowers and good persistence of the flower color without fading, recessed bright yellow flower stamens, exceptionally good hardiness to frost, unusually prolonged retention of the flower petals without dropping, a gradual opening habit of the flowers beginning at the bottom of each spike, and a strong and pleasing flower fragrance.

No references cited.